United States Patent [19]

Grabley et al.

[11] 4,389,488
[45] Jun. 21, 1983

[54] PROCESS FOR THE ENZYMATIC PREPARATION OF L-2-AMINO-4-METHYLPHOSPHINOBUTYRIC ACID

[75] Inventors: Susanne Grabley, Kelkheim; Klaus Sauber, Bad Soden am Taunus, both of Fed. Rep. of Germany

[73] Assignee: Hoechst Aktiengesellschaft, Frankfurt am Main, Fed. Rep. of Germany

[21] Appl. No.: 332,852

[22] Filed: Dec. 21, 1981

[30] Foreign Application Priority Data

Dec. 23, 1980 [DE] Fed. Rep. of Germany ........ 3048612

[51] Int. Cl.$^3$ ..................... C07B 19/02; C12P 13/04; C12R 1/19

[52] U.S. Cl. .................................. 435/280; 435/106; 435/849

[58] Field of Search .............................. 435/280, 106

[56] References Cited

U.S. PATENT DOCUMENTS 4,226,941 10/1980 Goi et al. ............................. 435/280

OTHER PUBLICATIONS

Plaskie et al., Journal of Antibiotics vol. 31, No. 8, pp. 783–783 (Aug. 1978).

Primary Examiner—Lionel M. Shapiro
Attorney, Agent, or Firm—Curtis, Morris & Safford

[57] ABSTRACT

A process for the enzymatic preparation of L-2-amino-4-methylphosphinobutyric acid by enzymatic cleavage of the corresponding N-arylacetyl derivatives using penicillin-G-acylase.

5 Claims, No Drawings

PROCESS FOR THE ENZYMATIC PREPARATION OF L-2-AMINO-4-METHYLPHOSPHINOBUTYRIC ACID

L-2-Amino-4-methylphosphinobutyric acid (in the following designated either L-phosphinothricine or L-PTC) or its salts with organic or inorganic bases or acids are, as is also known from German Offenlegungsschrift No. 2,939,269, the effective components of the racemates which are readily available chemically. According to German Offenlegungsschrift No. 2,717,440, these racemates show a very good and broad herbicidal activity against numerous monocotyledonous and dicotyledonous, annual and perennial weeds. Compared to the racemates, L-PTC and its abovementioned derivatives are approximately twice as effective, thus it was desirable to develop a process by means of which L-PTC would be made available in relatively large amounts.

L-PTC has already been obtained by acid hydrolysis (Japanese Published Application No. 73-85,538) or enzymatic degradation (Japanese Published Application No. 74-31,890) from L-PTC-alanylalanine, an antibiotic, known from the literature, which is produced microbially.

Furthermore, in German Offenlegungsschrift No. 2,939,269 a process is described in which N-acyl (in particular N-acetyl)-L-PTC is cleaved more quickly than the corresponding D derivative, using microbial acylases, which are employed in the form of whole cells or cell extracts and are derived from specially cultivated strains of the species Pseuodomonas, Streptomyces or Aspergillus. The acylase employed possess, according to the data in the German Offenlegungsschrift, hardly any or only a very slight activity for other substrates than N-acyl-L-PTC, for example for N-acyl derivatives of well-known usual L-aminoacids. The PTC isolated after work-up has, in addition, a maximum specific rotation $[\alpha]_D^{22}$ of only 23° (c=I, 1 N HCl), which corresponds to an optical purity of only about 75%.

However, investigations have shown that customary commercial acylases such as acylase I (aminoacylase from pigs' kidneys; EC 3.5.1.14) or microbial AMANO acylase, which are very suitable for cleavage of racemates of natural aminoacids, show no activity whatsoever for D,L-acyl-PTC. This confirms the data from German Offenlegungsschrift No. 2,939,269, according to which, a time-consuming microbiological screening is necessary for the production of PTC-active acylases by fermentation. Other enzymes, for example, proteolytic enzymes with esterase activity, which show high activity and selectivity with customary D,L-aminoacids, also possess only a very reduced activity or no activity for D,L-PTC esters.

Surprisingly, it has now been found that penicillin-G-acylase not only deacylates the phenacetyl derivative of D,L-PTC with an unusually high reaction rate, which approaches that in the deacylation of natural penicillin G, but also possesses a substantially increased selectivity in comparison to the microbial acylases described in German Offenlegungsschrift No. 2,939,269, which results in an extraordinarily high purity of the L-PTC formed.

Accordingly, the invention relates to a process for the enzymatic separation of D,L-2-amino-4-methylphosphinobutyric acid, which comprises treating its N-aracetyl derivatives of the formula

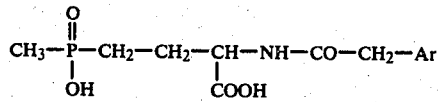

(in which Ar represents a phenyl radical which is optionally substituted by halogen or hydroxyl) with a penicillin-G-acylase in an aqueous or aqueous-organic medium.

It is in fact known that selective hydrolysis of certain phenacetylated normal D,L-aminoacids is possible with penicillin acylase derived from *E. coli*, to give free L-aminoacid (British Patent Specification No. 1,369,462; Bioorganiceskaja Khimia 5 (1979), 604 et seq.). However, it is also known that variations on the aminoacid part of the substrate lead to a large decrease of the enzymatic activity of the penicillin-G-acylase (A. Plaskie et al., J. Antiobiotics 31, 783 (1978)). Thus, it was unexpected that using the penicillin-G-acylases according to the invention, L-PTC can be obtained in high purity.

Using the process according to the invention a mixture of L-PTC and N-phenacetyl-D-PTC together with phenylacetic acid is produced, from which the L-PTC can be easily separated off in a known manner. For example, the aqueous reaction solution, if necessary after filtration, can be run through a column which is packed with a strong acid cation exchanger resin in the H(+)form. N-Phenacetyl-D-PTC and phenylacetic acid pass through the column, but the L-PTC is adsorbed on the resin. Elution can then be carried out in the known manner with dilute hydrochloric acid or ammonia. The eluate can, if necessary, be purified with active charcoal and subjected to freeze-drying, or the concentrated eluate can be brought to crystallization.

Starting materials of the formula I are obtained by methods known per se, for example by reaction of the disodium salt of D,L-PTC with phenacetyl chloride at −5° C. to +5° C. with simultaneous addition of equimolar amounts of sodium hydroxide solution. The reaction mixture can be immediately subjected to cleavage; if desired, the N-phenacetyl-D,L-PTC can also be obtained in crystalline form by acidification with hydrochloric acid or sulfuric acid. The N-phenacetyl-D-PTC, which has not been enzymatically cleaved, can, after separation of the phenylacetic acid using ether or dichloromethane, be converted into D-PTC by hydrolysis in dilute hydrochloric acid at 80° C., and after conversion into the racemate, can again be subjected to enzymatic cleavage.

Penicillin acylases or amidases are defined as those enzymes which can cleave penicillin to 6-aminopenicillanic acid. The penicillin-G-acylases suitable for the process according to the invention are produced by procaryotic micro-organisms such as *Escherichia coli, Bacillus megatherium* and the like (M. Cole et al., Meth. Enzym. 43, 698 (1975)) and are known under the E.C. No. 3.5.1.11. Penicillin-G-amidase from *E. coli* ATCC 11,105 is particularly preferred.

The penicillin-G-acylase used according to the invention can be employed either as a free, water-soluble lyophilisate or in a water-insoluble form bound to a carrier (cf. German Offenlegungsschrift No. 2,732,301) in an aqueous solution, which can contain a concentration of substrate of between 0.1 and 20%, preferably 4 to 6%. The reaction temperature lies between 10° C. and 60° C., preferably between 20° C. and 40° C., and the reaction takes 1–48 hours, depending on the substrate and enzyme concentration or enzyme activity. Sufficient enzymatic activity can be observed at a pH from 3 to 9, preferably at 6–8. The reaction can be carried out in a phosphate buffer or also without addition of a buffer. The reaction with carrier-bound enzyme can be carried out by batch or column procedures. In the column procedure, the enzyme is fixed as the stationary phase in the column and a solution of the substrate is continuously run through until complete deacylation of the N-aracetyl-L-PTC.

The course and end of the reaction can be followed by means of polarimetric methods or methods known from the literature for the quantitative analysis of the free aminoacid formed by reaction with ninhydrin and spectrophotometric determination of the content.

L-PTC obtained in high yield has a rotation value $[\alpha]_D^{22} = +28.5°$ (c=1 in 1 N HCl), which corresponds to an optical purity of at least 90% (corresponding to 95% of L form).

The following list of Examples serve to illustrate the invention further.

EXAMPLE 1

10 g (33.4 mmoles) of N-phenacetyl-D,L-PTC were suspended in a little double-distilled water, the pH was adjusted to 7.8 with 1 N NaOH, and the solution was made up to a volume of 500 ml with double-distilled water. After addition of 15 mg of penicillin-G-acylase from *E. coli* (activity approx. 2.9 U/mg; substrate penicillin-G potassium salt, reaction temperature 37° C.) the reaction mixture was allowed to stand at room temperature. After 15 hours, an approx. 50% conversion was found by determination of the content of free aminoacid by color reaction of a sample with ninhydrin. After acidification with concentrated hydrochloric acid to a pH of 2–3 and filtration, the clear, aqueous solution of substrate was run through a column, which was packed with 150 g Dowex® 50 W×2 (H+ form). It was washed with water until the eluate was neutral and chloride ions were no longer detectable. The free aminoacid was then eluted as the hydrochloride with 0.8 N hydrochloric acid in ethanol/water 80:20. The eluate was concentrated and pure PTC hydrochloride with a melting point of 199°–200° C. was obtained. Yield: 3.3 g (15.2 mmoles $\triangleq$ 45.4%). The free crystalline L-aminoacid was isolated from the hydrochloride in the usual manner, by addition of approx. double the molar amount of propylene oxide to the ethanolic solution of the substrate: melting point 217°–219° C., $[\alpha]_D^{22} = +28°$ (c=1, 1 N HCl).

EXAMPLE 2

60 g (200.5 mmoles) of N-phenacetyl-D,L-PTC were suspended in a little water, the pH was adjusted to 8.0 with sodium hydroxide solution, the volume was made up to 1 liter with water, and treated with 6 g of bound penicillin-G-acylase (activity approx. 80 U/g, substrate penicillin-G potassium salt, reaction temperature 37° C.; preparation of the carrier German Offenlegungsschrift No. 2,732,301). After stirring at room temperature for 1.5 days, the substrate solution was filtered off from the water-insoluble catalyst, and the filtrate was run over a column which was filled with 750 g of strongly acid cation exchanger resin, and further worked-up analogously to the reaction solution used in Example 1. 20 g (92 mmoles $\triangleq$ 46%) of L-PTC hydrochloride were obtained with a melting point of 199°–201° C. The specific angle of rotation $[\alpha]_D^{22}$ was determined as 23.3° (c=0.6, 1 N HCl) corresponding to a molar rotation of $[M]_D^{22} = 50.7$. The free L-PTC obtained after treatment with propylene oxide had a melting point of 216°–217° C. and a specific angle of rotation of $[\alpha]_D^{22} = +28.5°$ (c=1, 1 N HCl) corresponding to a molar rotation $[M]_D^{22}$ of 51.6°.

EXAMPLE 3

To test the stability of the carrier-bound penicillin-G-acylase used in Example 2 towards N-phenacetyl-D,L-PTC, 100 mg of the bound enzyme were treated with 10 ml of a 5% strength aqueous solution of N-phenacetyl-D,L-PTC (pH 7.8, stabilized by addition of a little phosphate buffer) and stirred at room temperature. After every 24 hours, the substrate solution was filtered off and the separated water-insoluble enzyme again treated with racemic substrate solution. The enzyme activity was measured by determination of the content of free PTC after 45 minutes and after 22.5 hours using the color reaction of a sample with ninhydrin.

After 8 weeks, no significant decrease of the PTC constituent was measurable after 45 minutes reaction (about 20%, based on added racemate). In every case, after 22.5 hours, 50% of the added racemate was hydrolyzed.

We claim:
1. A process for the enzymatic separation of D,L-2-amino-4-methylphosphinobutyric acid, which comprises treating its N-aracetyl derivatives of the formula

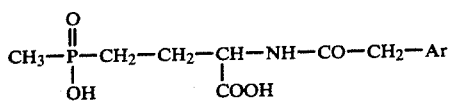

(in which Ar represents a phenyl radical which is optionally substituted by halogen or hydroxyl) in an aqueous or aqueous-organic medium with a penicillin-G-acylase.

2. A process as claimed in claim 1, wherein penicillin-G-acylase from *E. coli* is employed.

3. A process as claimed in any one of claims 1 and 2, wherein penicillin-G-acylase from *E. coli* ATCC 11,105 is employed.

4. A process as claimed in any one of claims 1 to 3 wherein the penicillin-G-acylase is in the form of a free lyophilisate.

5. A process as claimed in any one of claims 1 to 3, wherein the penicillin-G-acylase is bound to a carrier.

* * * * *